United States Patent
Yuki et al.

(10) Patent No.: US 9,833,407 B2
(45) Date of Patent: Dec. 5, 2017

(54) **NASAL VACCINE FOR *STREPTOCOCCUS PNEUMONIAE***

(71) Applicant: LSIP, LLC, Tokyo (JP)

(72) Inventors: Yoshikazu Yuki, Tokyo (JP); Hiroshi Kiyono, Tokyo (JP); Kazunari Akiyoshi, Kyoto (JP); Shinichi Sawada, Kyoto (JP)

(73) Assignee: Intellectual Property Strategy Network, Inc., Tokyo (JP)

( * ) Notice: Subject to any disclaimer, the term of this patent is extended or adjusted under 35 U.S.C. 154(b) by 0 days.

(21) Appl. No.: 15/119,335

(22) PCT Filed: Feb. 16, 2015

(86) PCT No.: PCT/JP2015/054146
§ 371 (c)(1),
(2) Date: Aug. 16, 2016

(87) PCT Pub. No.: WO2015/122518
PCT Pub. Date: Aug. 20, 2015

(65) Prior Publication Data
US 2017/0014338 A1 Jan. 19, 2017

(30) Foreign Application Priority Data
Feb. 17, 2014 (JP) .................. 2014-027205

(51) Int. Cl.
| A61K 39/09 | (2006.01) |
| A61K 39/02 | (2006.01) |
| A61K 39/00 | (2006.01) |
| A61K 9/00 | (2006.01) |
| A61K 9/06 | (2006.01) |
| A61K 47/36 | (2006.01) |

(52) U.S. Cl.
CPC .............. *A61K 9/0043* (2013.01); *A61K 9/06* (2013.01); *A61K 39/092* (2013.01); *A61K 47/36* (2013.01); *A61K 2039/543* (2013.01); *A61K 2039/552* (2013.01); *A61K 2039/55555* (2013.01)

(58) Field of Classification Search
CPC ......... A61K 39/00; A61K 39/02; A61K 39/09
USPC .................. 424/184.1, 234.1, 244.1
See application file for complete search history.

(56) References Cited

U.S. PATENT DOCUMENTS

2011/0206729 A1* 8/2011 Akiyoshi ................. A61K 9/06
424/204.1

FOREIGN PATENT DOCUMENTS

| JP | 5344558 | 11/2013 |
| WO | WO-00/12564 | 3/2000 |

OTHER PUBLICATIONS

Ayame, H., et al. Bioconjugate Chemistry, vol. 19, pp. 882-890, 2008.*
Yuki, Y., et al. The Journal of Immunology, vol. 188 (1 Supplement) abstract 166.7, May 2012.*
Berry et al., "Reduced Virulence of a Defined Pneumolysin-Negative Mutant of *Streptococcus pneumoniae*," Infect Immun 57: 2037-2042 1989.
McDaniel et al., "Use of Insertional Inactivation to Facilitate Studies of Biological Properties of Pneumococcal Surface Protein A (PspA)" J Exp Med 165: 381-394 1987.
Briles et al., "Intranasal Immunization of Mice with a Mixture of the Pneumococcal Proteins PsaA and PspA Is Highly Protective against Nasopharyngeal Carriage of *Streptococcus pneumoniae*" Infect Immun 68: 796-800 2000.
Nguyen et al., "Intranasal immunization with recombinant PspA fused with a flagellin enhances cross-protective immunity against *Streptococcus pneumoniae* infection in mice" Vaccine 29: 5731-5739 2011.
McCool et al., "The Immune Response to Pneumococcal Proteins during Experimental Human Carriage" J Exp Med 195: 359-365 2002.
Ayame et al., "Self-Assembled Cationic Nanogels for Intracellular Protein Delivery" Bioconjug Chem 19: 882-890 2008.
Nochi et al., "Nanogel antigenic protein-delivery system for adjuvant-free intranasal vaccines" Nat Mater 9: 572-578 2010.
Yuki et al., "Nanogel-based antigen-delivery system for nasal vaccines" Biotechnol Genet Eng Rev 29: 61-72 2013.
Kong et al., "Nanogel-Based PspA Intranasal Vaccine Prevents Invasive Disease and Nasal Colonization by *Streptococcus pneumoniae*" Infect Immun 81 : 1625-1634 2013.
Fukuyama, Y. et al., "Nanogel-based PspA nasal vaccine induces microRNA-associated protective immunity in nonhuman primates (MUC4P.834)," Mucosal Immunology Feb. 11, 2015: 1-10.
Fukuyama, Y. et al., "Nanogel-based PspA nasal vaccine induces S. pneumoniae-specific neutralizing antibody immune responses in nonhuman primates," Proceedings of the Japanese Society for Immunology vol. 42 Proceedings, 2013: 124, 2-C-W28-8-0.
Sato, A. et al. Clinical Microbiology, 2011, vol. 38, No. 3: 273-277 (partial English translation).
International Preliminary Report on Patentability for PCT/JP2015/054146 dated Mar. 24, 2015.

* cited by examiner

*Primary Examiner* — Rodney P Swartz
(74) *Attorney, Agent, or Firm* — Foley & Lardner LLP

(57) ABSTRACT

The present invention provides a nasal vaccine for *Streptococcus pneumoniae*, and a production method therefor. This nasal vaccine formulation for primates includes a complex of PspA, i.e. the vaccine antigen, and a nanogel in which hydrophobic cholesterol is added, as side chains, to pullulan having amino groups. Furthermore, the present invention provides a production method for the nasal vaccine formulation for primates.

4 Claims, 9 Drawing Sheets

FIG. 2

|  | $D_H{}^*$ (PDI**) | ZETA-POTENTIAL |
|---|---|---|
| cCHP20 | 31.1 nm (0.179) | +2.8 mV |
| PspA/cCHP20 | 31.1 nm (0.176) | +1.3 mV |

# NASAL VACCINE FOR *STREPTOCOCCUS PNEUMONIAE*

RELATED APPLICATIONS

This application is a U.S. National Stage of International Patent Application Number PCT/JP2015/054146, filed Feb. 16, 2015, which claims priority to Japanese Patent Application Number 2014-027205, filed Feb. 17, 2014. The entire contents of the foregoing applications are hereby incorporated herein by reference for all purposes.

TECHNICAL FIELD

The present invention relates to a nasal vaccine against *Streptococcus pneumoniae*.

BACKGROUND ART

Similar to influenza virus, *Streptococcus pneumoniae* is a pathogen of clinical importance that begins as an upper respiratory tract infection. The pathogenicity arises upon progression to otitis media, pneumonia, bacteremia, or meningitis. The manifestations are severe diseases that would result in death in children and adults.

As a method of preventing such an infection caused by *Streptococcus pneumoniae*, currently, 7-, 10- and 13-valent polysaccharide conjugate pneumococcal vaccines (PCV7, 10, 13) have been developed for adults and are delivered by intramuscular injection. However, such vaccines based on polysaccharides hardly induce an immune response in children due to low immunogenicity of polysaccharides as a T cell-independent antigen, and exhibit an infection-preventing effect only for *Streptococcus pneumoniae* of capsular types. Further, intramuscular injection of vaccines mainly induces systemic anti-IgG antibodies, thus causing such a problem that these vaccines fail to induce a mucosal immune response against *Streptococcus pneumoniae*.

PspA, the pneumococcal surface protein, is a well-known highly immunogenic protein and is considered to be a promising vaccine candidate (Non-Patent Literatures 1 and 2). It is present on virtually all strains of pneumococci, and PspA-based vaccines induce cross-reactive antibodies in mice and humans (Non-patent Literatures 3-5). Moreover, PspA-specific mucosal and systemic antibody responses are induced, and these responses are mediated by both Th1- and Th2-type cytokine responses by CD4$^+$ T cells in infant mice (via maternal immunization), as well as in aged mice. These findings indicate that PspA is a potent pneumococcal vaccine effective not only in adults but also in children.

*Streptococcus pneumoniae* of any types colonize the nasal cavity and cause an initial infection on the respiratory tract mucosae, thus a nasal vaccine is expected to be the most effective method for preventing *Streptococcus pneumoniae* infection.

However, there is currently no safe adjuvant for nasal immunization or delivery system of the nasal vaccine, as evaluated by the so-called safety pharmacology studies, such as absorption, distribution, metabolism and excretion (ADME), in preclinical studies, thus causing one of obstacles for practical application. Further, co-administration of biologically active mucosal adjuvants such as cholera toxin (CT) and heat-labile enterotoxin (LT) is facing concern that toxin may be delivered to the central nervous system or accumulated in the olfactory bulbs and the like. As such, administration of such adjuvants to humans is not very desirable and there are still matters to be solved on safety.

To overcome these concerns, the inventors of the present invention recently developed an effective vaccine delivery system with a self-assembled nanosized hydrogel (nanogel), which is composed of a cationic type of cholesteryl group-bearing pullulan (cCHP) (Patent Document 1, and Non-Patent Literature 6).

cCHP nanogel retains antigen proteins in its nano matrix and functions as an artificial chaperone that prevents antigens from aggregating and denaturing and assists refolding after releasing them. This cCHP nanogel is efficiently delivered to cells, and induces immune responses as an adjuvant-free vaccine (Non-Patent Literature 7, 8, and Patent Document 2). Furthermore, any experimental result did not show that nasally administered cCHP nanogel carrying the [111In]-labeled BoHc/A (non-toxic region of C-terminal heavy chain domain of botulinum neurotoxin type A) accumulates in the central nervous system including an olfactory bulb and a brain in mice (Non-Patent Literature 7). A separate study by the inventors demonstrated that a nasal PspA-nanogel vaccine is safe and induces strong antigen-specific systemic and mucosal antibody immune responses in mice (Non-Patent Literature 9).

As described above, the PspA-nanogel nasal vaccine is very excellent in terms of both safety and induction of protective immunity, and expected to be put in practical application as a nasal vaccine (Non-Patent Document 9). However, the efficacy has not been so far demonstrated in primates and further improvements have to be made for practical application.

CITATION LIST

Patent Documents

Patent Document 1: WO00/12564

Patent Document 2: JP 5344558B

Non-Patent Literatures

Non-Patent Literature 1: Berry et al., Infect Immun 57:2037-2042 1989

Non-Patent Literature 2: McDaniel et al., J Exp Med 165: 381-394 1987

Non-Patent Literature 3: Briles et al., Infect Immun 68:796-800 2000

Non-Patent Literature 4: Nguyen et al., Vaccin 29:5731-5739 2011

Non-Patent Literature 5: McCool et al., J Exp Med 195: 359-365 2002

Non-Patent Literature 6: Ayame et al., Bioconjug Chem 19:882-890 2008

Non-Patent Literature 7: Nochi et al., Nat Mater 9:572-578 2010

Non-Patent Literature 8: Yuki et al., Biotechnol Genet Eng Rev 29:61-72 2013

Non-Patent Literature 9: Kong et al., Infect Immun 81:1625-1634 2013

SUMMARY OF INVENTION

Technical Problem

In view of the above situation, an object of the present invention is to provide a safe and effective nasal vaccine for *Streptococcus pneumoniae* in primates.

Solution to Problem

The present inventors have conducted their earnest studies on a composition of the conventional PspA-nanogel vaccine in order to solve the above-mentioned problem and succeeded in inducing a protective immunity function against an infection with *Streptococcus pneumoniae* in primates by making improvements described below.

The inventors first increased a cationization rate of a nanogel (20 amino groups per 100 glucose units) and optimized a ratio of PspA and the nanogel (PspA (25 µg):nanogel (1.1 mg)=1:5 molar ratio).

Specifically, the present invention provides the following (1) to (4).

(1) A nasal vaccine formulation for primates, comprising a complex of a nanogel in which hydrophobic cholesterol is added, as side chains, to pullulan having an amino group, and PspA serving as a vaccine antigen, the nanogel having the amino group added at a ratio of 18 to 22 per 100 glucose units.

(2) The nasal vaccine formulation for primates according to the above (1), wherein the nanogel has the amino group added at a ratio of 20 per 100 glucose units.

(3) The nasal vaccine formulation for primates according to the above (1) or (2), wherein the PspA and the nanogel form a complex at a molar ratio of 1:4 to 1:6.

(4) A production method of a nasal vaccine formulation for primates, comprising a step of mixing: a nanogel in which hydrophobic cholesterol is added, as side chains, to pullulan having an amino group added at a ratio of 18 to 22 per 100 glucose units; and PspA, at a molar ratio of the PspA and the nanogel of 1:4 to 1:6.

Effects of Invention

According to the present invention, provided is a vaccine for *Streptococcus pneumoniae*, which induces protective immunity in primates in a safe and effective manner. Furthermore, an amount of the vaccine necessary for inducing protective immunity in mice can be reduced to about one-fifth of the value previously reported (see the aforementioned Non-Patent Document 9). In addition, by comparison to the previously reported vaccine (Non-Patent Document 9) in terms of the physicochemical characteristics, it can be confirmed that the vaccine has perfect FRET (fluorescence response energy transfer). Thus, it becomes possible to provide the nanogel vaccine that has improved stability in the characteristics.

Perfect FRET was detected from a complex of rhodamine-conjugated cCHP and FITC-conjugated PspA including them in optimized proportion (FITC-PspA/cCHP20-Rho) (A), in contrast, FRET was detected but insufficient under the previously published conditions (Non-Patent Literature 9) (B). Furthermore, FRET was not detected from FITC-conjugated naked PspA (FITC-PspA) or rhodamine-conjugated naked cCHP (cCHP20-Rho).

FIG. 2 Physicochemical property of the PspA-nanogel according to the present invention (Dynamic light scattering analysis and zeta-potential measurement)

Dynamic light scattering analysis ($D_H$(PDI)) showed that the cCHP nanogel particles were still of uniform size after the incorporation of PspA. FIG. 2 depicts measurement results of the zeta-potentials of cCHP-nanogel alone and the PspA-cCHP complex (Zeta-potential). *: Hydrodynamic diameter ($D_H$), **: Polydispersity index (PDI)

Figure 3:
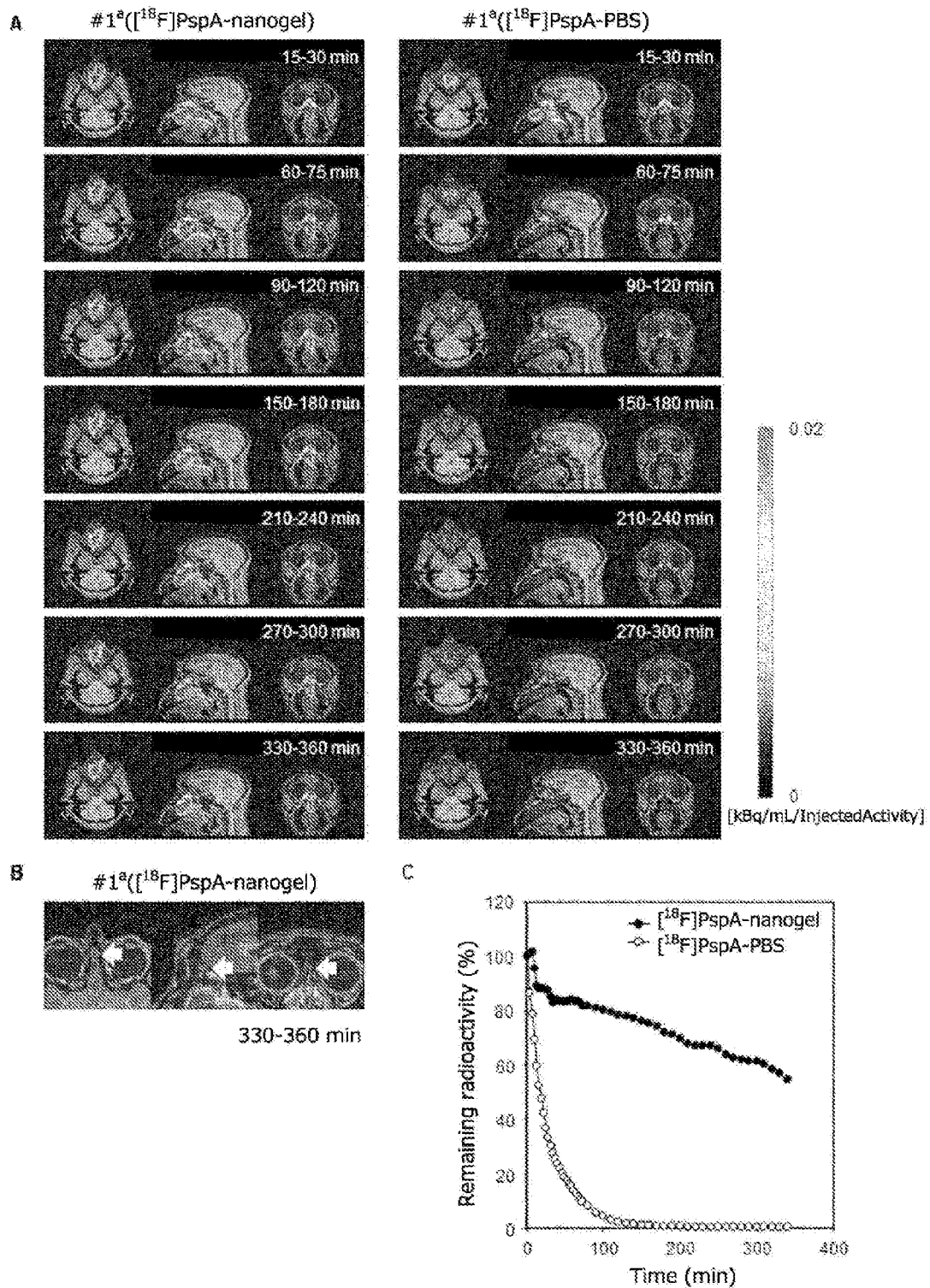

FIG. 3 PET/MRI images (A and B) and TACs (C) for nasal administration of [$^{18}$F]PspA-nanogel or [$^{18}$F]-PspA-PBS in a macaque. (A) After nasal administration of [$^{18}$F]-PspA-nanogel or [$^{18}$F]-PspA-PBS in a naive rhesus macaque, the macaque's head was scanned for 6 hours with a PET scanner. Real-time PET images overlaid on MRI images are shown for the indicated times post-administration. (B) To further check whether [$^{18}$F]-PspA accumulated in the central nervous system or the olfactory bulb, PET images were taken. (C) TACs (Time-activity curves) for the nasal cavity for the 6-hour period after nasal administration of [$^{18}$F]-PspA-nanogel or [$^{18}$F]-PspA-PBS are presented. The data are expressed as percentages of the dose remaining after nasal administration. a: The same macaque was nasally administered of [$^{18}$F]-PspA-nanogel or [$^{18}$F]-PspA-PBS with a 1-week interval between administrations.

Figure 4:
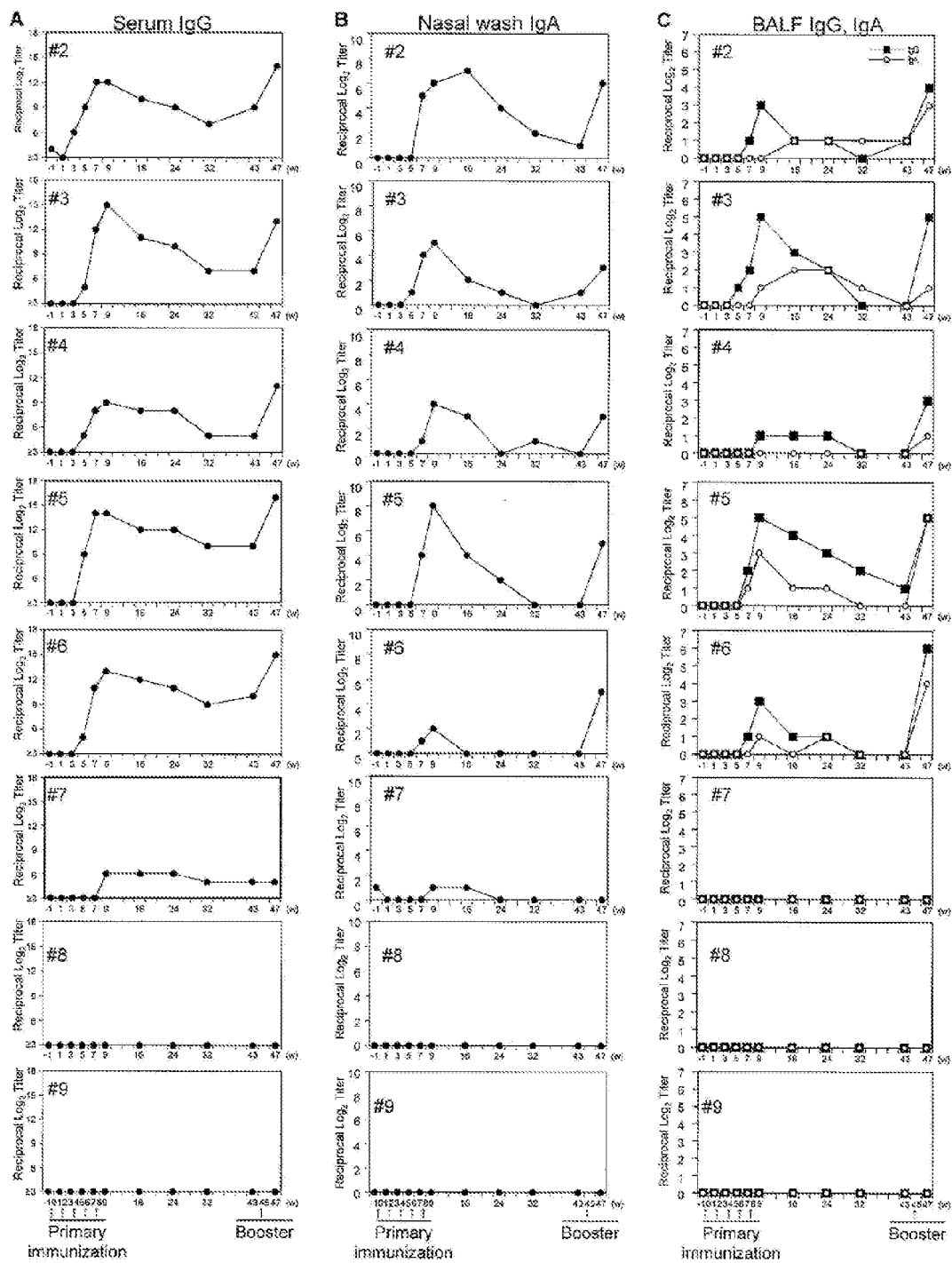

FIG. 4 Induction of immune responses after administration of PspA-nanogel in macaques Each cynomolgus macaque was nasally immunized with 2.5 µg PspA-nanogel (PspA:nanogel=1.5 molar ratio), PspA alone or PBS only at the times indicated with arrows, and serum, nasal wash, and bronchoalveolar lavage fluid (BALF) were collected. Then the levels of PspA-specific serum IgA (A), nasal wash IgA (B), and bronchoalveolar lavage fluid IgG (■) and IgA (○) (C) were determined by ELISA. #2-6: PspA-nanogel administration groups, #7, 8: PspA alone administration groups, #9: PBS administration groups.

Figure 5:
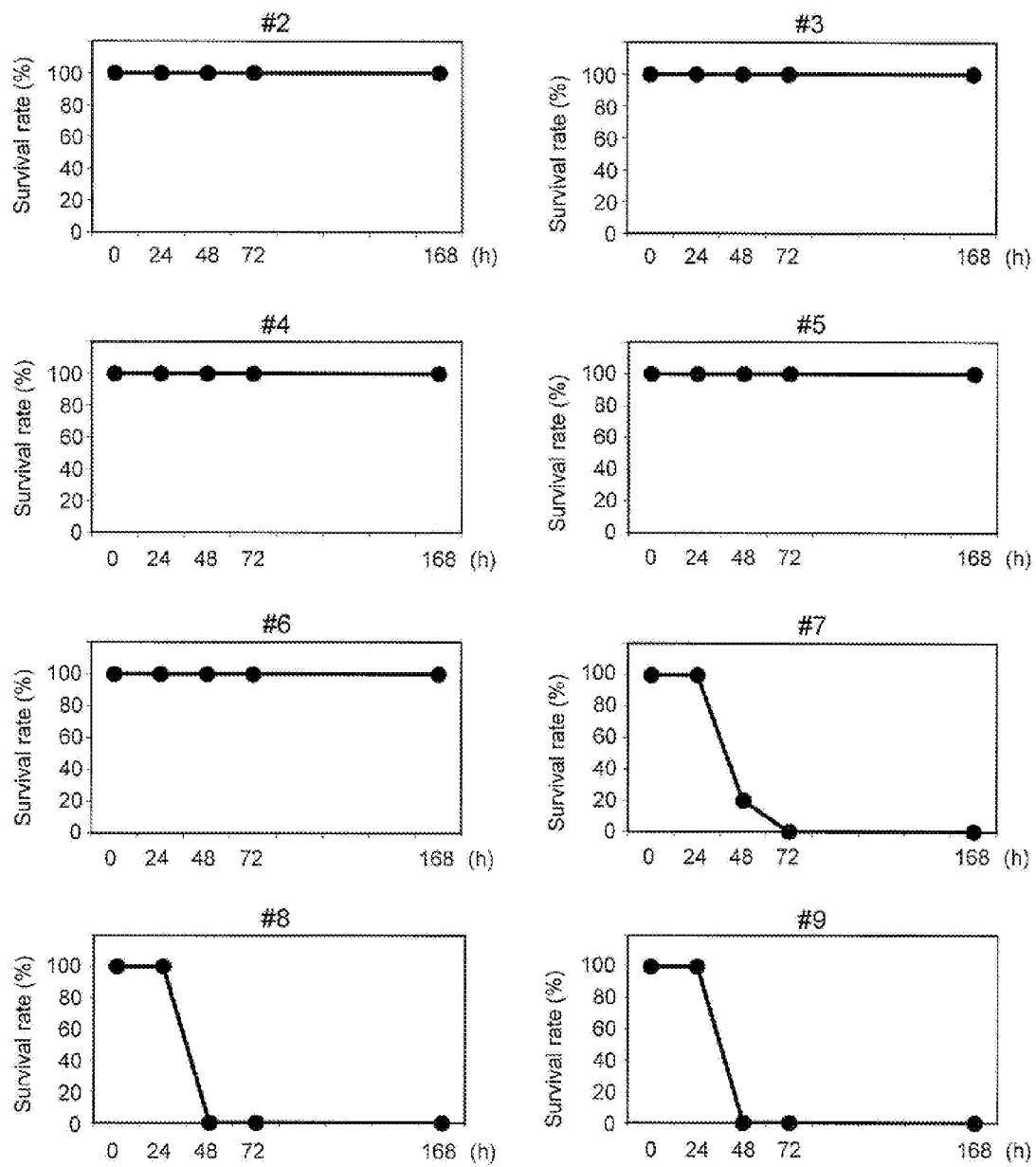

FIG. 5 Induction of protective immunity by administration of PspA-nanogel To evaluate the protective effect against *S. pneumoniae*, sera from immunized macaques were transferred to naïve BALB/c mice. Serum from each of the macaques was prepared 1 week after the final primary nasal immunization (PspA-nanogel (#2-6), PspA alone (#7, 8), or PBS only (#9)). Each serum aliquot was incubated at 37° C. for 1 hour with 7.5×10$^3$ CFU *S. pneumoniae* Xen 10 and intraperitoneally injected into mice. The mice were monitored daily for mortality.

Figure 6:
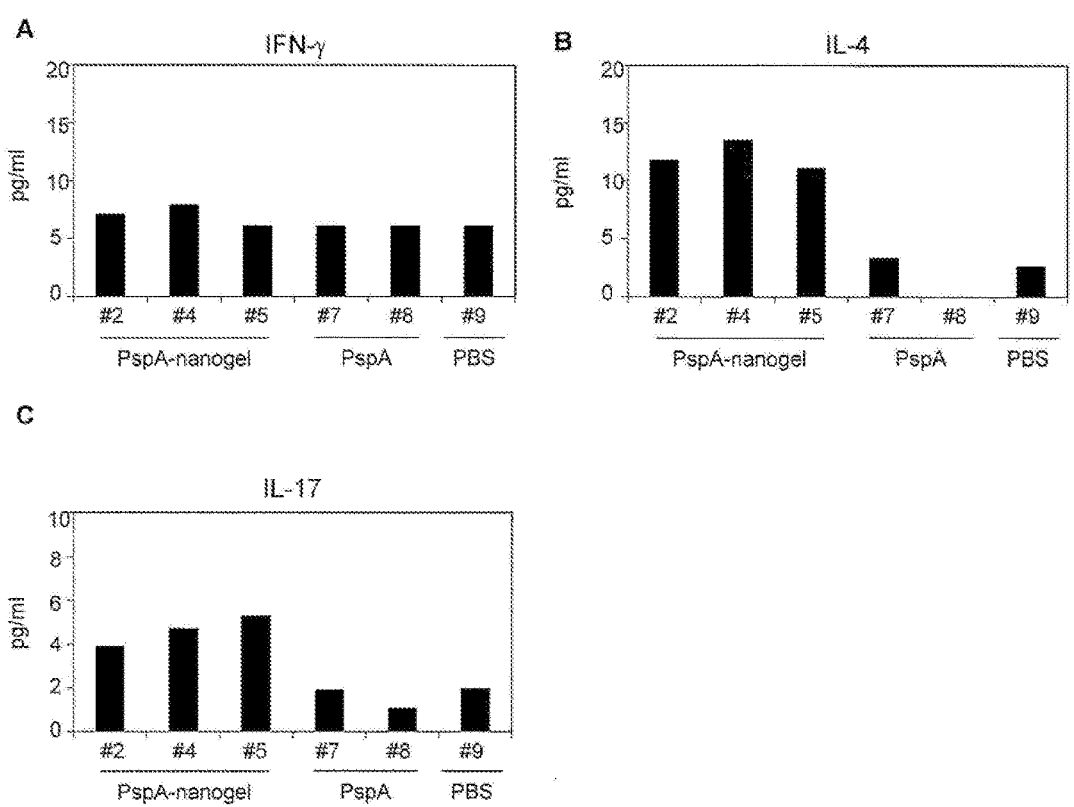

FIG. 6 Th2- and Th17-type cytokine production from CD4$^+$ T cells in PspA-nanogel immunized macaques CD4$^+$ T cells were separated from the peripheral blood mononuclear cells 1 week after the booster. Lymphocytes were cultured, along with irradiated APCs and 5 µg/ml of PspA with anti-CD28 and CD49d antibodies for 5 days. The levels of IFN-γ (A), IL-4 (B), and IL-17A (C) in the supernatants were measured. This experiment was repeated in triplicate. #2, 4, 5: PspA-nanogel administration groups, #7, 8: PspA alone administration groups, #9: PBS administration groups. In macaques #3 and #6, the peripheral blood mononuclear cells could not be separated.

Figure 7:
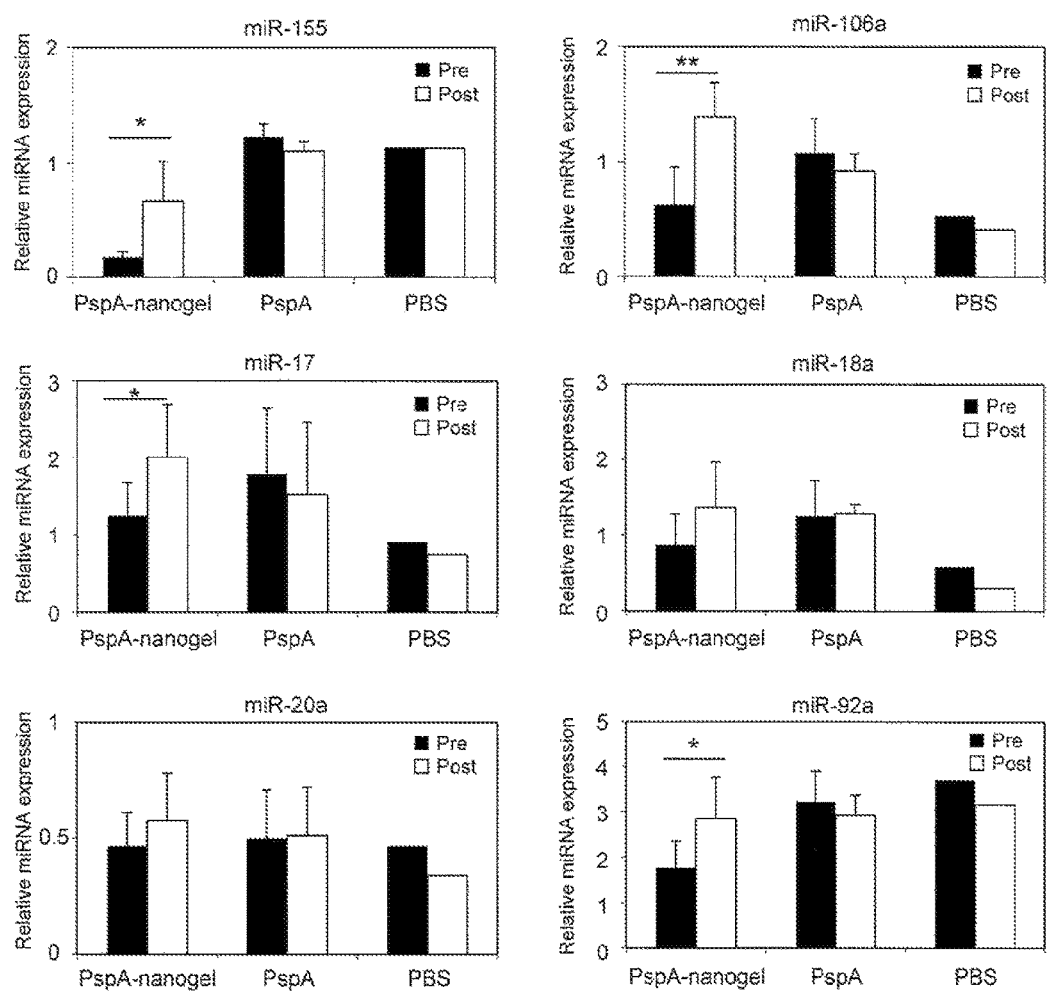

FIG. 7 MiRNA expression levels in macaques nasally immunized with PspA-nanogel

Expression levels of miR-155, miR-106a, miR-17, miR-18a, miR-20a, miR-92a in sera are shown. Expression levels of the indicated miRNA were analyzed by quantitative RT-PCR and normalized to the levels of miR-16. Values are shown as the means±standard deviation in each experimental group. *; p<0.05, **; p<0.01 when compared between pre-immunization and post-booster groups.

Figure 8:
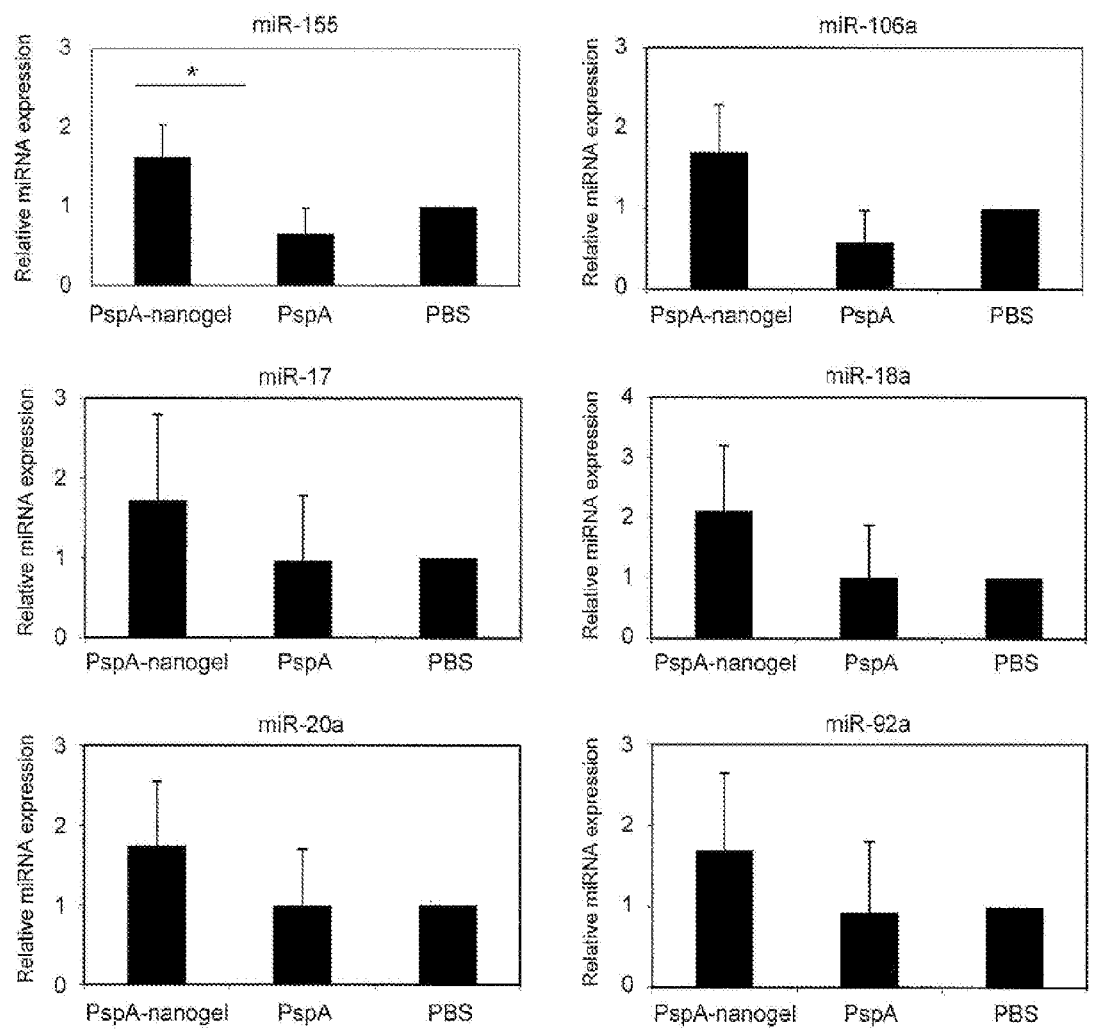

FIG. 8 MiRNA expression levels in macaques nasally immunized with PspA-nanogel

Expression levels of miR-155, miR-106a, miR-17, miR-18a, miR-20a, miR-92a in nasal tissues are shown. Expression levels of the indicated miRNA were analyzed by quantitative RT-PCR and normalized to the levels of miR-16. Values are shown as the means±standard deviation in each experimental group. *; p<0.05 when compared between pre-immunization and post-booster groups.

Figure 9:
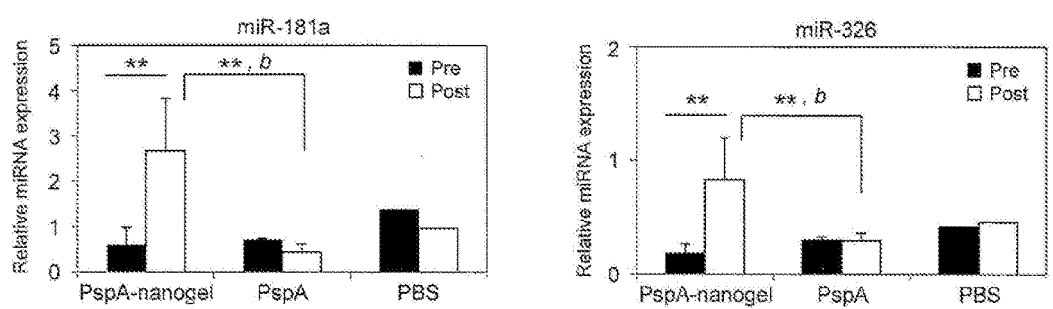
Figure 9:
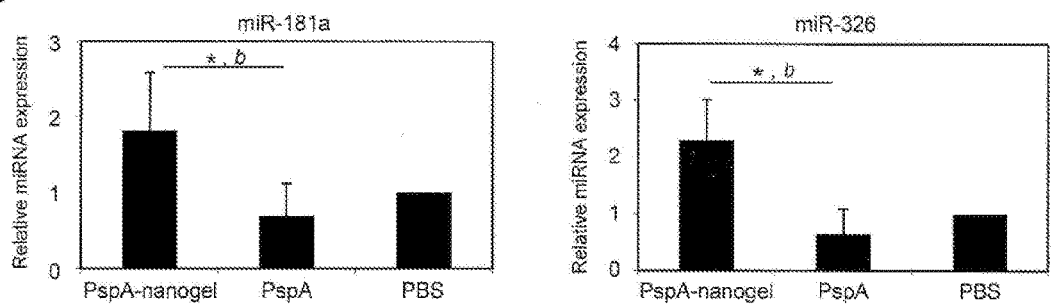

FIG. 9 MiRNA expression levels in macaques nasally immunized with PspA-nanogel

Expression levels of miR-326 and miR-181a in sera (A) and in nasal tissues (B) are shown. Expression levels of the indicated miRNA were analyzed by quantitative RT-PCR and normalized to the levels of miR-16. Values are shown as the means±standard deviation in each experimental group. *; p<0.05, **; p<0.01 when compared between pre-immunization and post-booster groups. b: Compared between PspA-nanogel and PspA or PBS groups in post-booster macaques. Pre; Sera of pre-immunization groups, Post; Sera of post-immunization groups.

DESCRIPTION OF EMBODIMENTS

By considering the situation where an effective nasal vaccine against an infection caused by Streptococcus pneumoniae has not been developed in primates including humans, the present invention has been completed by improving a previously reported PspA-nanogel vaccine and producing a nasal vaccine that effectively induces protective immunity in primates.

Specifically, one embodiment of the present invention is a nasal vaccine formulation for primates, comprising a complex of a nanogel in which hydrophobic cholesterol is added, as side chains, to pullulan having an amino group, and PspA serving as a vaccine antigen, the nanogel having the amino group added at a ratio of 18 to 22 per 100 glucose units.

In this description, the nanogel refers to a polymer gel nanoparticle comprising a hydrophilic polysaccharide (e.g., pullulan) with hydrophobic cholesterol added thereto as side chains. The nanogel can be produced based on a method described in, for example, WO 00/12564.

Specifically, a hydroxyl group-containing hydrocarbon or sterol having 12 to 50 carbon atoms is first allowed to react with a diisocyanate compound represented by OCN-R1 NCO (wherein R1 represents a hydrocarbon group having 1 to 50 carbon atoms) to produce an isocyanate group-containing hydrophobic compound containing one molecule of the hydroxyl group-containing hydrocarbon or the sterol having 12 to 50 carbon atoms is reacted. The resulting isocyanate group-containing hydrophobic compound is allowed to react with a polysaccharide to produce a hydrophobic group-containing polysaccharide that contains a hydrocarbon or steryl group having 12 to 50 carbon atoms. Next, the obtained product is purified with a ketone-based solvent to produce a high-purity hydrophobic group-containing polysaccharide.

In this description, pullulan, amylopectin, amylose, dextran, hydroxyethyl dextran, mannan, levan, inulin, chitin, chitosan, xyloglucan, or water-soluble cellulose may be used as the polysaccharide, and pullulan is particularly preferable.

Examples of the nanogel being used in the present invention include cholesterol-bearing pullulan (hereinafter referred to as CHP) and a CHP derivative. CHP has a structure wherein 1 to 10, preferably 1 to several, cholesterol molecules are added by substitution per 100 glucose units of pullulan having a molecular weight of 30,000 to 200,000, for example, 100,000. An amount of cholesterol substitution in the CHP used in the present invention may be suitably changed depending on the size and the degree of hydrophobicity of the antigen. In order to vary the degree of hydrophobicity of the CHP, one or more alkyl groups (having 10 to 30, preferably about 12 to 20 carbon atoms) may be added. The nanogels being used in the present invention have a particle size of 10 to 40 nm, preferably 20 to 30 nm. The nanogel is already commonly commercialized and such a commercialized nanogel may be used in the present invention.

The present invention uses a nanogel into which a positively charged functional group, for example, an amino group, has been introduced, so that a vaccine can be infiltrated into the nasal mucosa surface, which tends to be negatively charged. An optimum value of introduction rate of the amino groups in the nanogel depends on the antigen. When PspA is the antigen, the optimal range is 18 to 22, particularly preferably 20, per 100 glucose units of the CHP. As a method for introducing amino groups into the nanogel, a method involving the use of cholesterol pullulan (CHPNH$_2$) having amino groups added thereto can be mentioned.

Specifically, the CHP dried under a reduced pressure (0.15 g, as an example) is dissolved in 15 ml of dimethyl sulfoxide (DMSO) and 1-1'-carbonyldiimidazole (75 mg, as an example) is added thereto under a nitrogen stream, and then the reaction is allowed to proceed at room temperature for several hours (about 1 hour, as an example). Ethylenediamine (300 mg, as an example) is gradually added to the reaction solution and the mixture is stirred for about several to several tens of hours (about 24 hours, as an example). The resulting reaction solution is dialyzed against distilled water for several days. The reaction solution after dialysis is freeze-dried to obtain an opalescent solid. The degree of ethylenediamine substitution can be evaluated by an elemental analysis, H-NMR and the like.

The nasal vaccine for primates against Streptococcus pneumoniae of the present invention uses PspA (pneumococcal surface protein A) as an antigen. PspA is classified into family 1-3 and Glade 1-6, however any PspA can be used provided that it has antigenicity. Furthermore, a part of PspA having antigenicity may be used (a peptide consisting of amino acid positions 1 to 302 of mature PspA, as an example). Moreover, PspA being used as an antigen may also contain a peptide not derived from PspA (e.g., a tagging peptide for purification) unless it results in an adverse effect such as lowering the antigenicity of PspA. Examples of an amino acid sequence of PspA include SEQ ID No: 1 (an amino acid sequence containing a signal sequence; while SEQ ID No: 2 represents one example of coding nucleic acid sequence thereof) and SEQ ID No: 3 (an amino acid sequence of mature PspA; while SEQ ID No: 4 represents an example of coding nucleic acid sequence thereof). However the amino acid sequences of PspA are not limited by these examples. Those skilled in the art can readily acquire that information by conducting a search using public databases (such as the one provided by NCBI).

The nasal vaccine for primates of the present invention is the first nasal vaccine being produced that can be used in primates against infectious diseases caused by Streptococcus pneumoniae.

Primates described herein refer to the Primates order in the classification of animals and include humans and sub-human primates, as well as prosimians (lemurs, lorisids, and aye-aye), Old World monkeys, New World monkeys, and the like.

The complex of PspA serving as a vaccine antigen and the above cationic nanogel can be produced by making the cationic nanogel and PspA coexist and interact with each other, thus incorporating PspA into the cationic nanogel. Producing a complex is referred to as complex formation. As for the mixing ratio of PspA and the cationic nanogel, they can, for example, be mixed at 1:4 to 1:6, preferably 1:5, in terms of a molar ratio of PspA:nanogel.

The complex of PspA and nanogel is formed by mixing PspA and the nanogel in a buffer and allowing the mixture to stand at 4 to 50° C., for example, 46° C., for 30 minutes to 48 hours, for example, about 1 hour. The buffer used for the complex formation of PspA and the nanogel is not particularly limited. For example, the buffer used for forming a vaccine antigen-cationic nanogel complex can be suitably prepared in accordance with a type of protein and nanogel. Suffice it to say, a Tris-HCl buffer (50 mM, pH 7.6) can be mentioned as an example. The prepared PspA-nanogel complex may be analyzed for physicochemical characteristics by a known method. For example, such an analysis may be performed with fluorescence response energy transfer (FRET), dynamic light scattering (DLS), and measurement of zeta potentials.

The nasal vaccine preparation of the present invention is administered by application to the nasal mucosa. As its method, for example, the preparation can be administered into the nasal cavity by a spraying, coating, or dropping operation to the nasal mucosa. The nasal vaccine of the present invention induces a systemic immune response to produce IgGs specific to Streptococcus pneumoniae in the body and, at the same time, a mucosal immune response to produce IgA antibodies in the mucosa. Thus, by both the systemic and the mucosal immune systems, infections can be prevented and infectious diseases can be treated.

The nasal vaccine preparation may contain a known pharmaceutically acceptable stabilizer, antiseptic, antioxidant, and the like. Examples of such stabilizers include gelatin, dextran, and sorbitol. Examples of the antiseptic include thimerosal and β-propiolactone. Examples of the antioxidant include α-tocopherol.

A dose of the mucosal vaccine preparation can be suitably determined based on age and body weight of the subject, as long as it contains a pharmaceutically effective amount of the vaccine antigen. The term "pharmaceutically effective amount" refers to an amount of an antigen that is necessary for inducing an immune response to the vaccine antigen. For example, a single dose of several μg to several tens of mg of a vaccine antigen may be administered once to several times per day. Moreover, days of administration may vary from one to five or more, at intervals of one day to several weeks.

The present invention will be described further in detail by way of Examples below without being restricted thereto by any means.

EXAMPLE

1. Materials and Methods
1-1 Animals

Eight female naive cynomolgus macaques (Macaca fascicularis, 5 years old, ~3 kg) were used for the immunization study and were maintained at the Tsukuba Primate Research Center for Medical Science at the National Institute of Biomedical Innovation (NIBIO, Ibaraki, Japan). Also, one naive male rhesus macaque (Macaca mulatta, 5-6 years old, ~5 kg) was used for the PET imaging study, which was conducted at PET Center of Hamamatsu Photonics K.K. To assay antibody neutralization, female BALB/c mice (6 weeks old) were purchased from Japan SLC (Shizuoka, Japan) and used. All experiments were performed in accordance with the Guidelines for Use and Care of Experimental Animals, and the protocol was approved by the Animal Committee of NIBIO, Hamamatsu Photonics K.K., and The University of Tokyo.

1-2. Preparation of Recombinant PspA

Recombinant PspA of S. pneumoniae Rx1 (family 1, Glade 2) (an amino acid sequence of a coding region thereof is set forth in SEQ ID NO.1, and an amino acid sequence of a mature protein thereof is set forth in SEQ ID NO.3) was prepared as described previously (see Briles et al., Infect Immun 68:796-800, 2000), with slight modification. In brief, the plasmid encoding PspA/Rx1 (GenBank accession no. M74122, pUAB055) was used to transform E. coli BL21 (DE3) cells. To construct pUAB055, a 909-bp fragment of PspA from a pneumococcal strain Rx1 was cloned into the pET20b vector (Novagen) between the NcoI and XhoI sites. Recombinant PspA/Rx1 contains the first 302 amino acids of mature PspA plus six polyhistidines at the C-terminal end.

The cultured E. coli cells were harvested and sonicated, and then the sonicated cell supernatant was loaded onto a DEAE-Sepharose column (BD Healthcare). Then it was loaded onto a Ni affinity column (Qiagen) and the Recombinant PspA was purified by gel filtration on a Sephadex G-100 column (BD Healthcare). Endotoxin contents were less than or equal to 0.05 EU/mg.

1-3. Preparation of Recombinant PspA-nanogel Complex

The cCHP nanogel (~40 nm size) generated from cationic type of cholesteryl group-bearing pullulan was used for all experiments. This cCHP nanogel contained 20 amino groups per 100 glucose units. The PspA-cCHP complex for each immunization was prepared by mixing PspA (25 μg) with cCHP (1.1 mg) at a 1:5 molecular ratio and incubating for 1 hour at 46° C. Fluorescence response energy transfer (FRET) was determined with an FP-6500 fluorescence spectrometer (JASCO) with FITC-conjugated PspA and TRITC-conjugated cCHP nanogel (Ayame et al., Bioconjug Chem 19:882-890 2008: Nochi et al., Nat Mater 9:572-578 2010). Furthermore, Dynamic light scattering (DLS) and the zeta-potential of cCHP carrying or not carrying, PspA was determined with a Zetasizer Nano ZS instrument (Malvern Instruments).

1-4. Nasal Immunization to Macaques and Sample Collection

Cynomolgus macaques were nasally immunized five times at 2-week intervals with PspA-nanogel under ketamine anesthesia. For the control group, macaques were nasally administered with 25 μg of PspA alone, or PBS only. Serum, nasal wash (NW), and bronchoalveolar lavage fluid (BALF) were collected before primary immunization, 1 week after each immunization, 2, 4, 6, and 8 months after the final immunization, and 2 weeks after receipt of the booster.

1-5. Analysis of PspA-specificity on Antibody Responses

The antigen-specific antibody responses were analyzed by ELISA (Kong et al., Infect Immun 81:1625-1634, 2013). 96-well plates were coated with 1 μg/ml PspA in PBS overnight at 4° C. After blocking with 1% BSA in PBS-Tween, twofold serial dilutions of samples were added and incubated for 2 hours at room temperature. After washing of the samples, HRP-conjugated goat anti-monkey IgG (Nordic Immunological Laboratory) or HRP-conjugated goat anti-monkey IgA (Cortex Biochem) diluted 1:1,000 was added and incubated for 2 hours at room temperature. After the incubation, the color was developed with the use of TMB Microwell Peroxidase Substrate System (XPL). End-point titers were expressed as (reciprocal log 2 titer) which is logarithm of the last dilution that gave an $OD_{450}$ of at least 0.1 greater than the negative control.

1-6. Bacterial Strain

The kanamycin-resistant pneumococcal strain S. pneumonia Xen10 (Caliper Life Sciences) was used in this experiment. This strain was derived from the wild type strain A66.1, which expresses PspA of family 1, clades 1 and 2. The virulence of *S. pneumoniae* Xen10 is comparable with that of the parent strain. The *S. pneumoniae* Xen10 was grown in brain heart infusion (BHI) broth at 37° C. in 5% $CO_2$.

1-7. Neutralizing Activity of Sera from Vaccinated Cynomolgus Macaques

To evaluate neutralizing activity against the PspA antigen in a serum prepared from cynomolgus macaques that had received the vaccine, serum was prepared from individual cynomolgus macaques immunized by PspA-nanogel, PspA alone, or PBS only. 10 µl of the each serum sample was incubated with $7.5 \times 10^3$ CFU of a *S. pneumoniae* Xen 10 in 90 µl solution at 37° C. for 1 hour. Subsequently, each mixture was injected intraperitoneally into a Balb/c mouse (100 µl per mouse) which was monitored for one week.

1-8. PspA-Specific $CD4^+$ T-Cell Responses

One week after the macaques had received the booster, lymphocytes were prepared from the peripheral blood by using Ficoll-Paque PLUS (GEHealthcare). From the washed lymphocytes, $CD4^+$ T cells were purified by using CD4 microbeads and magnetic cell sorting (AutoMACS). $CD8^+$ T cells were also purified in the same manner. The cells remaining after the removal of $CD4^+$ and $CD8^+$ T cells were used as antigen-presenting cells (APCs) after irradiation at 3,000 rad. $CD4^+$ T cells ($1 \times 10^5$ cells/well) and APCs ($0.5 \times 10^5$ cells/well) were resuspended in RPMI 1640 (Nacalai Tesque) supplemented with 10% FCS and penicillin-streptomycin (Gibco), and were cultured in 24-well plates in the presence of 5 µl/ml PspA with anti-CD28 (clone: CD28.2) and anti-CD49d (clone: 9F10) antibodies (0.5 µg/ml each) (eBioscience) at 37° C. in 5% $CO_2$. Supernatants were then collected. The concentrations of the cytokines, IFN-γ, IL-4, and IL-17 in the supernatants were measured with a Monkey Singleplex Bead Kit (Invitrogen) and Bio-Plex 200 (Bio-Rad).

1-9. Synthesis of $[^{18}F]$-PspA $[^{18}F]$-PspA was radiolabeled with N-succinimidyl-4-$[^{18}F]$ fluorobenzoate ($[^{18}F]$SFB). Purified PspA was radiolabeled by conjugating $[^{18}F]$SFB to free amino groups, including the N-terminal and ε-Lys amino groups. The product was purified by gel-permeation chromatography (Superose 12, PBS, 1 ml/min). The 615 MBq $[^{18}F]$SFB was obtained at 150 min from the EOB (end of bombardment). The radiochemical purity and the decay-corrected radiochemical yield were 100% and 2.95%, respectively.

1-10. PET/MRI Imaging in Rhesus Macaques

Because the half-life of $[^{18}F]$ is only 110 min, nasal $[^{18}F]$-PspA-nanogel or $[^{18}F]$-PspA-PBS administration with a 1-week interval between administrations was given to the same naive macaque. After nasal administration of 50 MBq per 700 µl of $[^{18}F]$-PspA-nanogel or $[^{18}F]$-PspA-PBS (350 µl in each nostril), the macaque's head was tilted back for 10 min and then scanned in an upright position after anesthesia. PET scans were conducted for 345 min with frames of 25×3 min, followed by 27×10 min, with the use of a high-resolution animal PET scanner (SHR-7700) (Hamamatsu Photonics). MRI images were recorded with Signa Excite HDxt (3T) (GE Healthcare) to identify the cerebrum regions. Sensitivity of the PET was 0.05 SUV (standardized uptake value), which is almost the same level as conventional autoradiograms of indium $^{111}$In or iodine $^{125}$I.

1-11. Image Data Analysis

PET data were analyzed by means of the PMOD software package (PMOD Technologies). Each PET image was superimposed on the corresponding MRI data to identify the regions of the cerebrum. TACs (Time-activity curves) of PET/MRI images were expressed as % remaining dose.

1-12. MiRNA Microarray Analysis

The pre-immunized and post-booster serum samples were used for microarray analysis. Microarray analyses were performed by using the 3D-Gene miRNA microarray platform (TORAY). RNA extraction was performed according to the manufacturer's instructions. Total RNA was labeled with Hy5 and hybridized at 32° C. for 16 hours on the 3D-Gene human miRNA chip whose sequence had high homology with rhesus macaques or pigtail macaques. The oligonucleotide sequences of the probes were confirmed to the miRBase. MiRNA gene expression data were scaled by global normalization.

1-13. MiRNA Expression Levels in Serum and Nostril Tissues

Serum samples were prepared before primary immunization and after booster with PspA-nanogel, PspA alone, or PBS only. The nostril epithelial tissue samples were collected after booster immunization with PspA-nanogel, PspA alone, or PBS only. Total RNAs were isolated from serum by using TRIzol LS reagent, and from nostril tissue by using TRIzol reagent (Invitrogen). All the miRNAs in the sample were polyadenylated by using poly A polymerase and ATP. Following polyadenylation, SuperScript III RT and a Universal Primer (Invitrogen) were used to synthesize cDNA from the tailed miRNA population. Each of the first-strand cDNAs was analyzed by quantitative RT-PCR with Fast SYBR Green Master Mix and Step One Plus Real-Time PCR System (Applied Biosystems). The expression levels were normalized to miR-16, which is a commonly used internal control for miRNA expression.

1-14. Statistical Analysis

The results are presented as means±standard deviation (SD). Student's t-test was used for statistical comparisons among groups. The p values<0.05 or <0.01 were considered to indicate statistical significance.

2. Results 2-1. Complex of PspA and Cationic Nanogel (cCHP)

In the present experiments, the nanogel being used contained 20 amino groups per 100 glucose units, and the preparation was made by mixing 2.5 µg of PspA with cCHP at a molecular ratio of 1:5. By using such a preparation method, an antigen-specific immune response could be induced with one fifth of the amount used in the previously reported method (Kong et al., Infect Immun 81: 1625-1634 2013). It is noted that the PspA-nanogel vaccine prepared by the conventional method (Kong et al., Infect Immun 81: 1625-1634 2013) failed to induce the immune response in cynomolgus macaques.

Figure 1:
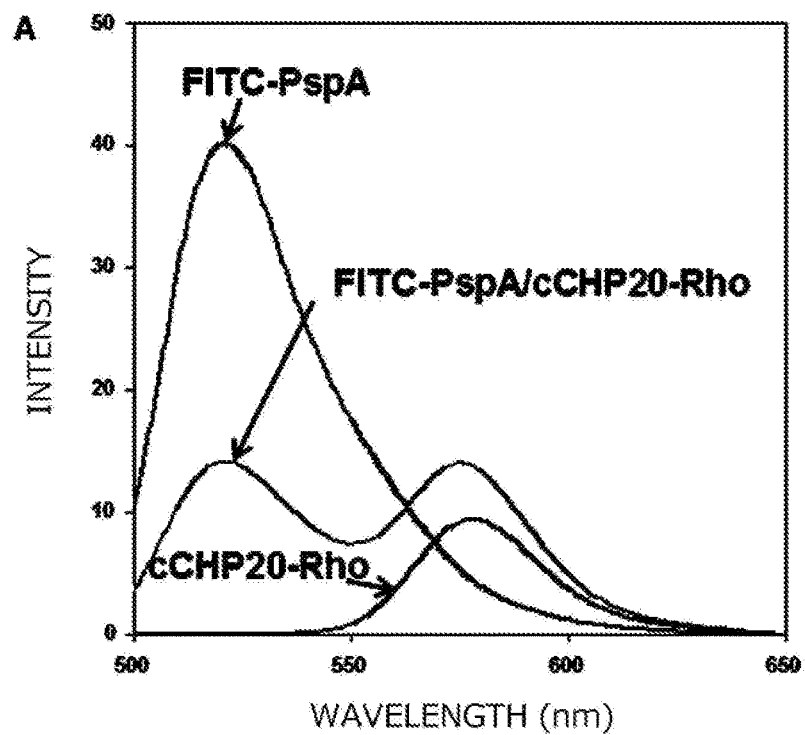
FIG. 1 Physicochemical property of the PspA-nanogel according to the present invention (FRET analysis)
Figure 1:
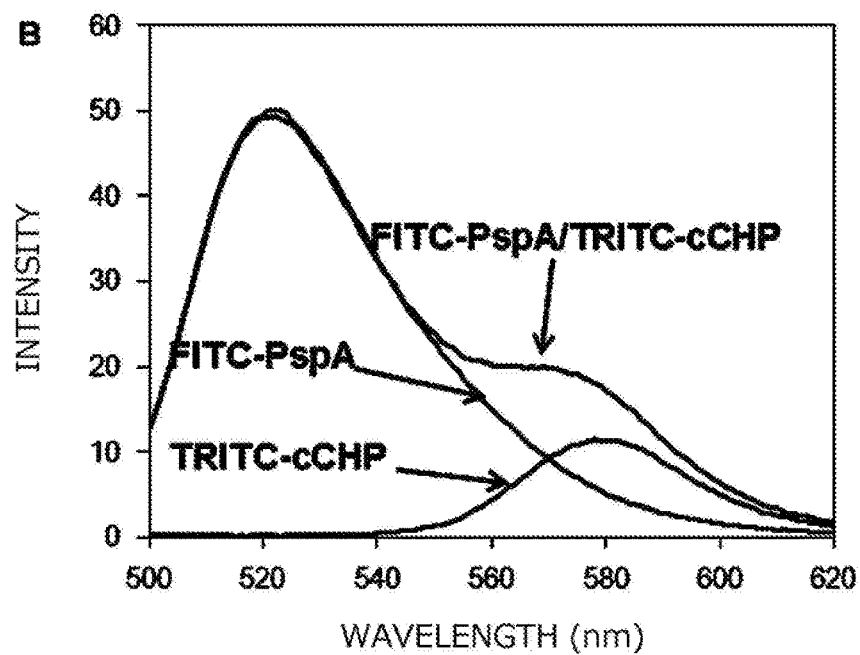

First, complex formation and uniformity in size of nanometer scale of the PspA-nanogel was confirmed by FRET analysis (FIG. 1A) and dynamic light scattering (DLS) (FIG. 2). These showed that the nanogel uniformly formed a nanoparticle after incorporating PspA. In particular, FRET data of the optimized PspA-nanogel (FIG. 1A) showed a perfect FRET result as compared to previously reported data (FIG. 1B). Furthermore, following formation the complex had a positive zeta-potential, indicating that the PspA-nanogel was suitable for capturing a protein having efficacy (FIG. 2). These results demonstrate that the improved cCHP nanogel of the present invention can effectively deliver the vaccine antigen to the anionic nasal epithelium, thus allowing for nasal administration.

2-2. Effect of [$^{18}$F]-PspA-nanogel Nasal Administration

These studies were undertaken to assess retention of the PspA-nanogel in the nasal cavity and whether it accumulates in the olfactory bulbs or central nervous system.

After anesthetizing the macaques, the macaque's head was placed on the PET scanner and real-time imaging was performed for 6 hours. To confirm the exact position of the cerebrum, MRI scan was performed and then the MRI images were superimposed onto the PET images. FIG. 3A depicts real-time PET images of a rhesus macaque 15 minutes to 6 hours following nasal administration. The PET images clearly showed that nasally administered [$^{18}$F]-PspA-nanogel was effectively delivered to the nasal mucosa and retained in the nasal tissues for up to 6 hours (FIG. 3A left and FIG. 3C). In contrast, the free form of [$^{18}$F]-PspA without a nanogel had gradually disappeared from the nasal cavity by 3 hours after nasal administration (FIG. 3A right).

Furthermore, no deposition of vaccine antigen was detected in the cerebrum or olfactory bulbs of macaques, even 6 hours after nasal administration of [$^{18}$F]-PspA (FIG. 3B).

These results show that PspA-nanogel of the present invention is effective nasal vaccine delivery system and safe.

2-3. Mucosal and Systemic Immune Responses Induced by Nasal Administration of PspA-nanogel Next, whether administration of PspA-nanogel vaccine in to nasal cavity induces PspA-specific immune responses was examined. One week after the final immunization, PspA-specific serum IgG antibody responses were significantly increased in macaques nasally immunized with PspA-nanogel when compared with macaques administered with PspA alone or PBS only (FIG. 4A), and these response levels were gradually decreased. Similarly, PspA-specific bronchoalveolar lavage fluid IgG and nasal wash IgA antibody responses exhibited higher levels in macaques nasally immunized with PspA-nanogel when compared with macaques nasally immunized with PspA alone or PBS only (FIGS. 4B and 4C), and these antibody levels were also gradually decreased. In addition, PspA-specific bronchoalveolar lavage fluid IgA antibody responses were slightly increased in two of the immunized macaques (No. 3 and No. 5) (FIG. 4C).

When these macaques were given a dose of booster of PspA-nanogel 8 months after the final immunization, the levels of PspA-specific serum and bronchoalveolar lavage fluid IgG and nasal wash IgA antibody responses recovered to those observed after the initial PspA-nanogel immunization (FIGS. 4A-C). Furthermore, PspA-specific IgA antibody responses in bronchoalveolar lavage fluid of macaques of No. 2, No. 5 and No. 6, which were nasally immunized with PspA-nanogel, recovered more than those observed after the primary immunization (FIG. 4C).

These findings suggest that PspA-nanogel is therefore a promising nasal vaccine candidate that can induce long-lasting antigen-specific systemic and mucosal immunity and can elicit nasal booster activity.

2-4. Protective Immunity against *S. pneumoniae* Induced by Nasal Administration of PspA-nanogel To investigate whether the nasal PspA-nanogel vaccine induces protective immunity, whether serum from macaques nasally immunized with PspA-nanogel would passively protect against pneumococcal infection was examined. When Balb/c mice were injected with pooled sera of macaques challenged with *S. pneumoniae* Xen10 and nasally immunized with PspA-nanogel, mice were fully protected from infections for at least 1 week (FIG. 5, #2-6). In contrast, mice that received sera from macaques given nasal PspA alone (FIG. 5, #7,8) or PBS (FIG. 5, #9) only died within 3 days post-challenge.

These results demonstrated that protective immunity was induced by nasal PspA-nanogel vaccination.

2-5. Th2 and Th17 Responses Induced by Nasal Immunization with PspA-nanogel

As described above, As macaques nasally immunized with PspA-nanogel showed high IgG/IgA responses. Then next, the levels of cytokine production in CD4$^+$ T cells isolated from blood of the macaques were determined. Lymphocytes were prepared from blood of all the macaques except the macaques No. 3 and 6. The macaques No. 2, 4 and 5 nasally immunized with PspA-nanogel showed increased levels of IL-4 and IL-17 production by CD4$^+$ T cells when compared with macaques given PspA alone (#7 and 8) or PBS (#9) only (FIGS. 6B,6C). However, essentially identical levels of IFN-γ were produced by CD4$^+$ T cells in the groups nasally immunized with PspA-nanogel (No. 2, 4 and 5), PspA alone (No. 7 and 8), or PBS only (No. 9) (FIG. 6A). These results are in good correlation with the result that nasal immunization with PspA-nanogel induced PspA-specific IgG antibody responses, which is the hallmark of the Th2-type immune response. Furthermore, these results indicated that the nasal PspA-nanogel vaccine could induce Th2 cytokine response and Th17 cytokine response as well.

2-6. Correlation between nasal immunization with PspA-nanogel and the expression levels of miRNAs The expression state of miRNA following nasal immunization was next examined.

MiRNA microarray analysis was performed to identify immunologically associated differences in serum miRNA profiles between pre-immunized and post-boosted serum samples. Some immunologically relevant miRNAs were selected, namely miR-155, miR-181a, miR-326, miR-106a, miR-17, miR-18a, miR-20a, and miR-92a, and quantitative RT-PCR of them was performed (FIGS. 6, 7 and 8). MiRNA Expression levels of miR-155, miR-106a, miR-17, miR-18a, miR-20a, and miR-92a showed increasing trends in the sera and on the mucosal surfaces of macaques received a booster dose and macaques immunized with PspA-nanogel. These data indicate a T-cell, especially Th2 cell, immune response (FIGS. 7 and 8).

Expression levels of miR-326, Th17-cell differentiation-related miRNA, and miR-181a, T-cell and B-cell differentiation-related miRNA, were significantly increased in the sera of macaques given a nasal booster dose of PspA-nanogel when compared with control macaques as pre-immunization (FIG. 9A). The levels of the these miRNAs were also shown significantly higher on the mucosal surfaces of macaques immunized with PspA-nanogel than the levels on the mucosal surfaces of control macaques given PspA alone or PBS only (FIG. 9B). These results suggest that these miRNAs have important roles in Th17 cytokine responses and Th2 immune responses after nasal immunization with PspA-nanogel.

INDUSTRIAL APPLICABILITY

The nasal vaccine for *Streptococcus pneumoniae* of the present invention can effectively prevent an infection caused by *Streptococcus pneumoniae*. Thus, the present invention can be expected to be applicable in the field of preventive medicine related to infectious diseases.

The invention claimed is:

1. A nasal vaccine formulation for primates, comprising a complex of a nanogel in which hydrophobic cholesterol is added, as side chains, to pullulan having an amino group, and PspA serving as a vaccine antigen, the nanogel having the amino group added at a ratio of 18 to 22 per 100 glucose units,
wherein the PspA and the nanogel form a complex at a molar ratio of 1:4 to 1:6.

2. The nasal vaccine formulation for primates according to claim 1, wherein the nanogel has the amino group added at a ratio of 20 per 100 glucose units.

3. A production method for a nasal vaccine formulation for primates, comprising a step of mixing: a nanogel in which hydrophobic cholesterol is added, as side chains, to pullulan having an amino group added at a ratio of 18 to 22 per 100 glucose units; and PspA, at a molar ratio of the PspA and the nanogel of 1:4 to 1:6.

4. A nasal vaccine formulation for primates, comprising a complex of a nanogel in which hydrophobic cholesterol is added, as side chains, to pullulan having an amino group, and PspA serving as a vaccine antigen, the nanogel having the amino group added at a ratio of 20 per 100 glucose units, wherein the PspA and the nanogel form a complex at a molar ratio of 1:5.

* * * * *

SEQUENCE LISTING

<160> NUMBER OF SEQ ID NOS: 4

<210> SEQ ID NO 1
<211> LENGTH: 619
<212> TYPE: PRT
<213> ORGANISM: Streptococcus pneumoniae

<400> SEQUENCE: 1

```
Met Asn Lys Lys Lys Met Ile Leu Thr Ser Leu Ala Ser Val Ala Ile
1               5                   10                  15

Leu Gly Ala Gly Phe Val Ala Ser Gln Pro Thr Val Val Arg Ala Glu
            20                  25                  30

Glu Ser Pro Val Ala Ser Gln Ser Lys Ala Glu Lys Asp Tyr Asp Ala
        35                  40                  45

Ala Lys Lys Asp Ala Lys Asn Ala Lys Lys Ala Val Glu Asp Ala Gln
    50                  55                  60

Lys Ala Leu Asp Asp Ala Lys Ala Ala Gln Lys Lys Tyr Asp Glu Asp
65                  70                  75                  80

Gln Lys Lys Thr Glu Glu Lys Ala Ala Leu Glu Lys Ala Ala Ser Glu
                85                  90                  95

Glu Met Asp Lys Ala Val Ala Ala Val Gln Gln Ala Tyr Leu Ala Tyr
            100                 105                 110

Gln Gln Ala Thr Asp Lys Ala Ala Lys Asp Ala Ala Asp Lys Met Ile
        115                 120                 125

Asp Glu Ala Lys Lys Arg Glu Glu Ala Lys Thr Lys Phe Asn Thr
    130                 135                 140

Val Arg Ala Met Val Val Pro Glu Pro Glu Gln Leu Ala Glu Thr Lys
145                 150                 155                 160

Lys Lys Ser Glu Glu Ala Lys Gln Lys Ala Pro Glu Leu Thr Lys Lys
                165                 170                 175

Leu Glu Glu Ala Lys Ala Lys Leu Glu Glu Ala Glu Lys Lys Ala Thr
            180                 185                 190

Glu Ala Lys Gln Lys Val Asp Ala Glu Val Ala Pro Gln Ala Lys
        195                 200                 205

Ile Ala Glu Leu Glu Asn Gln Val His Arg Leu Glu Gln Glu Leu Lys
    210                 215                 220

Glu Ile Asp Glu Ser Glu Ser Glu Asp Tyr Ala Lys Glu Gly Phe Arg
225                 230                 235                 240

Ala Pro Leu Gln Ser Lys Leu Asp Ala Lys Lys Ala Lys Leu Ser Lys
                245                 250                 255

Leu Glu Glu Leu Ser Asp Lys Ile Asp Glu Leu Asp Ala Glu Ile Ala
            260                 265                 270

Lys Leu Glu Asp Gln Leu Lys Ala Ala Glu Glu Asn Asn Asn Val Glu
        275                 280                 285

Asp Tyr Phe Lys Glu Gly Leu Lys Thr Ile Ala Ala Lys Lys Ala
    290                 295                 300

Glu Leu Glu Lys Thr Glu Ala Asp Leu Lys Lys Ala Val Asn Glu Pro
305                 310                 315                 320

Glu Lys Pro Ala Pro Ala Pro Glu Thr Pro Ala Pro Glu Ala Pro Ala
                325                 330                 335

Glu Gln Pro Lys Pro Ala Pro Ala Pro Gln Pro Ala Pro Ala Pro Lys
            340                 345                 350

Pro Glu Lys Pro Ala Glu Gln Pro Lys Pro Glu Lys Thr Asp Asp Gln
        355                 360                 365
```

-continued

```
            Gln Ala Glu Glu Asp Tyr Ala Arg Arg Ser Glu Glu Tyr Asn Arg
                370                 375                 380

Leu Thr Gln Gln Gln Pro Pro Lys Ala Glu Lys Pro Ala Pro Ala Pro
            385                 390                 395                 400

Lys Thr Gly Trp Lys Gln Glu Asn Gly Met Trp Tyr Phe Tyr Asn Thr
                                405                 410                 415

Asp Gly Ser Met Ala Thr Gly Trp Leu Gln Asn Asn Gly Ser Trp Tyr
                            420                 425                 430

Tyr Leu Asn Ser Asn Gly Ala Met Ala Thr Gly Trp Leu Gln Tyr Asn
                        435                 440                 445

Gly Ser Trp Tyr Tyr Leu Asn Ala Asn Gly Ala Met Ala Thr Gly Trp
                450                 455                 460

Ala Lys Val Asn Gly Ser Trp Tyr Tyr Leu Asn Ala Asn Gly Ala Met
            465                 470                 475                 480

Ala Thr Gly Trp Leu Gln Tyr Asn Gly Ser Trp Tyr Tyr Leu Asn Ala
                                485                 490                 495

Asn Gly Ala Met Ala Thr Gly Trp Ala Lys Val Asn Gly Ser Trp Tyr
                            500                 505                 510

Tyr Leu Asn Ala Asn Gly Ala Met Ala Thr Gly Trp Leu Gln Tyr Asn
                        515                 520                 525

Gly Ser Trp Tyr Tyr Leu Asn Ala Asn Gly Ala Met Ala Thr Gly Trp
                530                 535                 540

Ala Lys Val Asn Gly Ser Trp Tyr Tyr Leu Asn Ala Asn Gly Ala Met
            545                 550                 555                 560

Ala Thr Gly Trp Val Lys Asp Gly Asp Thr Trp Tyr Tyr Leu Glu Ala
                                565                 570                 575

Ser Gly Ala Met Lys Ala Ser Gln Trp Phe Lys Val Ser Asp Lys Trp
                            580                 585                 590

Tyr Tyr Val Asn Gly Leu Gly Ala Leu Ala Val Asn Thr Thr Val Asp
                        595                 600                 605

Gly Tyr Lys Val Asn Ala Asn Gly Glu Trp Val
                610                 615

<210> SEQ ID NO 2
<211> LENGTH: 1860
<212> TYPE: DNA
<213> ORGANISM: Streptococcus pneumoniae

<400> SEQUENCE: 2
atgaataaga aaaaaatgat tttaacaagt ctagccagcg tcgctatctt agggggctggt      60 tttgttgcgt ctcagcctac tgttgtaaga gcagaagaat ctcccgtagc cagtcagtct     120
aaagctgaga agactatga tgcagcgaag aaagatgcta agaatgcgaa aaaagcagta     180
gaagatgctc aaaaggcttt agatgatgca aaagctgctc agaaaaaata tgacgaggat     240
cagaagaaaa ctgaggagaa agccgcgcta gaaaaagcag cgtctgaaga gatggataag     300
gcagtggcag cagttcaaca agcgtatcta gcctatcaac aagctacaga caaagccgca     360
aaagacgcag cagataagat gatagatgaa gctaagaaac gcgaagaaga ggcaaaaact     420
aaatttaata ctgttcgagc aatggtagtt cctgagccag cagttggc tgagactaag      480 aaaaaatcag aagaagctaa acaaaaagca ccagaactta ctaaaaaact agaagaagct     540
aaagcaaaat tagaagaggc tgagaaaaaa gctactgaag ccaaacaaaa agtggatgct     600
gaagaagtcg ctcctcaagc taaatcgct gaattggaaa atcaagttca tagactagaa     660
caagagctca agagattga tgagtctgaa tcagaagatt atgctaaaga aggtttccgt     720
```

```
gctcctcttc aatctaaatt ggatgccaaa aaagctaaac tatcaaaact tgaagagtta    780
agtgataaga ttgatgagtt agacgctgaa attgcaaaac ttgaagatca acttaaagct    840
gctgaagaaa acaataatgt agaagactac tttaaagaag gtttagagaa aactattgct    900
gctaaaaaag ctgaattaga aaaaactgaa gctgacctta agaaagcagt taatgagcca    960
gaaaaaccag ctccagctcc agaaactcca gccccagaag caccagctga caaccaaaa   1020 ccagcgccgg ctcctcaacc agctcccgca ccaaaaccag agaagccagc tgaacaacca   1080
aaaccagaaa aaacagatga tcaacaagct gaagaagact atgctcgtag atcagaagaa   1140
gaatataatc gcttgactca acagcaaccg ccaaaagctg aaaaaccagc tcctgcacca   1200
aaaacaggct ggaaacaaga aaacggtatg tggtacttct acaatactga tggttcaatg   1260
gcgacaggat ggctccaaaa caacggttca tggtactacc tcaacagcaa tggtgctatg   1320
gctacaggtt ggctccaata caatggttca tggtattacc tcaacgctaa cggcgctatg   1380
gcaacaggtt gggctaaagt caacggttca tggtactacc tcaacgctaa tggtgctatg   1440
gctacaggtt ggctccaata caatggttca tggtattacc tcaacgctaa cggcgctatg   1500
gcaacaggtt gggctaaagt caacggttca tggtactacc tcaacgctaa tggtgctatg   1560
gctacaggtt ggctccaata caacggttca tggtactacc tcaacgctaa cggtgctatg   1620
gctacaggtt gggctaaagt caacggttca tggtactacc tcaacgctaa tggtgctatg   1680
gcaacaggtt gggtgaaaga tggagatacc tggtactatc ttgaagcatc aggtgctatg   1740
aaagcaagcc aatggttcaa agtatcagat aaatggtact atgtcaatgg tttaggtgcc   1800
cttgcagtca acacaactgt agatggctat aaagtcaatg ccaatggtga atgggttaa    1860
```

<210> SEQ ID NO 3
<211> LENGTH: 588
<212> TYPE: PRT
<213> ORGANISM: Streptococcus pneumoniae

<400> SEQUENCE: 3

```
Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
                20                  25                  30

Gln Lys Ala Leu Asp Asp Ala Lys Ala Ala Gln Lys Lys Tyr Asp Glu
            35                  40                  45

Asp Gln Lys Lys Thr Glu Glu Lys Ala Ala Leu Glu Lys Ala Ala Ser
        50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Glu Ala Lys Thr Lys Phe Asn
                100                 105                 110

Thr Val Arg Ala Met Val Val Pro Glu Pro Glu Gln Leu Ala Glu Thr
            115                 120                 125

Lys Lys Lys Ser Glu Glu Ala Lys Gln Lys Ala Pro Glu Leu Thr Lys
        130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Glu Val Ala Pro Gln Ala
                165                 170                 175
```

```
Lys Ile Ala Glu Leu Glu Asn Gln Val His Arg Leu Glu Gln Glu Leu
                180                 185                 190

Lys Glu Ile Asp Glu Ser Ser Glu Asp Tyr Ala Lys Glu Gly Phe
            195                 200                 205

Arg Ala Pro Leu Gln Ser Lys Leu Asp Ala Lys Lys Ala Lys Leu Ser
        210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Asn Asn Asn Val
                245                 250                 255

Glu Asp Tyr Phe Lys Glu Gly Leu Glu Lys Thr Ile Ala Ala Lys Lys
                260                 265                 270

Ala Glu Leu Glu Lys Thr Glu Ala Asp Leu Lys Lys Ala Val Asn Glu
            275                 280                 285

Pro Glu Lys Pro Ala Pro Ala Pro Glu Thr Pro Ala Pro Glu Ala Pro
        290                 295                 300

Ala Glu Gln Pro Lys Pro Ala Pro Ala Pro Gln Pro Ala Pro Ala Pro
305                 310                 315                 320

Lys Pro Glu Lys Pro Ala Glu Gln Pro Lys Pro Glu Lys Thr Asp Asp
                325                 330                 335

Gln Gln Ala Glu Glu Asp Tyr Ala Arg Arg Ser Glu Glu Tyr Asn
                340                 345                 350

Arg Leu Thr Gln Gln Gln Pro Pro Lys Ala Glu Lys Pro Ala Pro Ala
        355                 360                 365

Pro Lys Thr Gly Trp Lys Gln Glu Asn Gly Met Trp Tyr Phe Tyr Asn
        370                 375                 380

Thr Asp Gly Ser Met Ala Thr Gly Trp Leu Gln Asn Asn Gly Ser Trp
385                 390                 395                 400

Tyr Tyr Leu Asn Ser Asn Gly Ala Met Ala Thr Gly Trp Leu Gln Tyr
                405                 410                 415

Asn Gly Ser Trp Tyr Tyr Leu Asn Ala Asn Gly Ala Met Ala Thr Gly
            420                 425                 430

Trp Ala Lys Val Asn Gly Ser Trp Tyr Tyr Leu Asn Ala Asn Gly Ala
        435                 440                 445

Met Ala Thr Gly Trp Leu Gln Tyr Asn Gly Ser Trp Tyr Tyr Leu Asn
450                 455                 460

Ala Asn Gly Ala Met Ala Thr Gly Trp Ala Lys Val Asn Gly Ser Trp
465                 470                 475                 480

Tyr Tyr Leu Asn Ala Asn Gly Ala Met Ala Thr Gly Trp Leu Gln Tyr
                485                 490                 495

Asn Gly Ser Trp Tyr Tyr Leu Asn Ala Asn Gly Ala Met Ala Thr Gly
            500                 505                 510

Trp Ala Lys Val Asn Gly Ser Trp Tyr Tyr Leu Asn Ala Asn Gly Ala
        515                 520                 525

Met Ala Thr Gly Trp Val Lys Asp Gly Asp Thr Trp Tyr Tyr Leu Glu
        530                 535                 540

Ala Ser Gly Ala Met Lys Ala Ser Gln Trp Phe Lys Val Ser Asp Lys
545                 550                 555                 560

Trp Tyr Tyr Val Asn Gly Leu Gly Ala Leu Ala Val Asn Thr Thr Val
                565                 570                 575

Asp Gly Tyr Lys Val Asn Ala Asn Gly Glu Trp Val
                580                 585
```

```
<210> SEQ ID NO 4
<211> LENGTH: 1764
<212> TYPE: DNA
<213> ORGANISM: Streptococcus pneumoniae

<400> SEQUENCE: 4
gaagaatctc ccgtagccag tcagtctaaa gctgagaaag actatgatgc agcgaagaaa      60
gatgctaaga atgcgaaaaa agcagtagaa gatgctcaaa aggctttaga tgatgcaaaa     120
gctgctcaga aaaatatga cgaggatcag aagaaaactg aggagaaagc cgcgctagaa     180
aaagcagcgt ctgaagagat ggataaggca gtggcagcag ttcaacaagc gtatctagcc     240
tatcaacaag ctacagacaa agccgcaaaa gacgcagcag ataagatgat agatgaagct     300
aagaaacgcg aagaagaggc aaaaactaaa tttaatactg ttcgagcaat ggtagttcct     360
gagccagagc agttggctga gactaagaaa aaatcagaag aagctaaaca aaaagcacca     420
gaacttacta aaaaactaga agaagctaaa gcaaaattag aagaggctga gaaaaaagct     480
actgaagcca aacaaaaagt ggatgctgaa gaagtcgctc ctcaagctaa aatcgctgaa     540
ttggaaaatc aagttcatag actagaacaa gagctcaaag agattgatga gtctgaatca     600
gaagattatg ctaagaagg tttccgtgct cctcttcaat ctaaattgga tgccaaaaaa     660
gctaaactat caaaacttga agagttaagt gataagattg atgagttaga cgctgaaatt     720
gcaaaacttg aagatcaact taaagctgct gaagaaaaca ataatgtaga agactacttt     780
aaagaaggtt tagagaaaac tattgctgct aaaaaagctg aattagaaaa aactgaagct     840
gaccttaaga aagcagttaa tgagccagaa aaaccagctc cagctccaga aactccagcc     900
ccagaagcac cagctgaaca accaaaacca gcgccggctc ctcaaccagc tcccgcacca     960
aaaccagaga agcagctga caaccaaaa ccagaaaaaa cagatgatca acaagctgaa    1020
gaagactatg ctcgtagatc agaagaagaa tataatcgct tgactcaaca gcaaccgcca    1080
aaagctgaaa aaccagctcc tgcaccaaaa acaggctgga acaagaaaa cggtatgtgg    1140 tacttctaca atactgatgg ttcaatggcg acaggatggc tccaaaacaa cggttcatgg    1200
tactacctca acagcaatgg tgctatggct acaggttggc tccaatacaa tggttcatgg    1260
tattacctca acgctaacgg cgctatggca acaggttggg ctaaagtcaa cggttcatgg    1320
tactacctca acgctaatgg tgctatggct acaggttggc tccaatacaa cggttcatgg    1380
tattacctca acgctaacgg cgctatggca acaggttggg ctaaagtcaa cggttcatgg    1440
tactacctca acgctaatgg tgctatggct acaggttggc tccaatacaa cggttcatgg    1500
tactacctca acgctaacgg tgctatggct acaggttggg ctaaagtcaa cggttcatgg    1560
tactacctca acgctaatgg tgctatggca acaggttggg tgaaagatgg agatacctgg    1620
tactatcttg aagcatcagg tgctatgaaa gcaagccaat ggttcaaagt atcagataaa    1680
tggtactatg tcaatggttt aggtgccctt gcagtcaaca caactgtaga tggctataaa    1740
gtcaatgcca atggtgaatg ggtt                                           1764
```